United States Patent

Jones, Jr. et al.

[11] Patent Number: 5,849,249
[45] Date of Patent: Dec. 15, 1998

[54] SOLID PHASE EXTRACTION APPARATUS FOR ENHANCED RECOVERY AND PRECISION

[75] Inventors: Walter Leon Jones, Jr., Asbury Park; Alfonso Liu, Boonton; James C. Robbins, Monmouth Junction; Joseph Stefkovich, Franklin, all of N.J.

[73] Assignee: Whatman Inc., Clifton, N.J.

[21] Appl. No.: 819,004

[22] Filed: Mar. 17, 1997

[51] Int. Cl.⁶ ........................................ B01D 29/05
[52] U.S. Cl. ................ 422/101; 210/406; 210/455; 210/496; 422/58
[58] Field of Search ................ 422/101, 56, 58; 210/266, 282, 299, 300, 317, 339, 406, 455, 473, 474, 475, 496, 502.1

[56] References Cited

U.S. PATENT DOCUMENTS

| | | | |
|---|---|---|---|
| 4,401,447 | 8/1983 | Huber | 210/282 |
| 5,186,831 | 2/1993 | DePetris | 210/502.1 |
| 5,375,477 | 12/1994 | Neill et al. | 210/406 |
| 5,407,575 | 4/1995 | Vinsonhaler | 210/502.1 |
| 5,529,694 | 6/1996 | Strickler | 422/107 |

*Primary Examiner*—Jan Ludlow
*Attorney, Agent, or Firm*—Mathews, Collins, Shepherd & Gould, P.A.

[57] ABSTRACT

In accordance with the invention, an SPE extraction apparatus is provided with a new SPE disk which eliminates radial wicking and weeping and new disk holding apparatus which minimizes the indirect flow region and minimizes the number of sample transfers required. The new SPE disk encapsulates the sorbent/fiber matrix between two porous outer layers which can be filters, united into an essentially non-porous rim around the disk perimeter. The disk holder and ring seal against this disk rim so that the active central portion of the disk is held entirely within the direct flow path. Thus weeping and indirect flow loss are virtually eliminated. In a preferred embodiment, the apparatus eliminates the need to manually disassemble the apparatus while in use. Advantageously a flow control mechanism is incorporated into the disk holder to further minimize the amount of solvent needed for extraction.

6 Claims, 7 Drawing Sheets

SOLID PHASE EXTRACTION APPARATUS FOR ENHANCED RECOVERY AND PRECISION

FIELD OF THE INVENTION

This invention relates to a solid phase extraction disk, disk holder and apparatus for providing enhanced recovery and precision.

BACKGROUND OF THE INVENTION

Solid phase extraction (SPE) is a well-established laboratory technique for analyzing liquid and mixed liquid/solid samples. The basic objective of such apparatus is to filter the solid portion of the sample (if any) and to selectively adsorb compounds from the liquid portion onto a sorbent. The analyte of interest can be subsequently extracted from the solvent and eluted from the sorbent with a minimal amount of an appropriate solvent.

Typical conventional SPE disk apparatus disposes a thin sorbent-impregnated SPE disk between the flange of an upper funnel and the flange of a lower base. Sample is poured into the funnel, and a vacuum source is applied to the base to draw sample through the disk. From time to time the vacuum source is disconnected, a number of manual manipulations and transfers are performed and extraction solvent is applied to the disk to remove analyte adsorbed within.

Unfortunately this apparatus loses analyte of interest and lacks precision. It loses analyte because of lateral wicking to the periphery of the disk and weeping out the edges. In addition, analyte can be lost through manual transfers of the solvent containing the analyte into different sample containers. It lacks precision because analyte wicked toward periphery can be lost to analysis even if it does not reach the edges. If the material wicks into the region between the flanges, it moves out of the direct flow region where it can be extracted into an indirect flow (dead) region where it is not extracted in conventional practice. Accordingly there is a need for an improved SPE apparatus.

SUMMARY OF THE INVENTION

In accordance with the invention, an SPE extraction apparatus is provided with a new SPE disk which eliminates radial wicking and weeping and new disk holding apparatus which minimizes the indirect flow region and minimizes the number of sample transfers required. The new SPE disk encapsulates the sorbent/fiber matrix between two porous outer layers which can be filters, united into an essentially non-porous rim around the disk perimeter. The disk holder and ring seal against this disk rim so that the active central portion of the disk is held entirely within the direct flow path. Thus weeping and indirect flow loss are virtually eliminated. In a preferred embodiment, the apparatus eliminates the need to manually disassemble the apparatus while in use. Advantageously a flow control mechanism is incorporated into the disk holder to further minimize the amount of solvent needed for extraction.

BRIEF DESCRIPTION OF THE DRAWINGS

The advantages, nature and various additional features of the invention will appear more fully upon consideration of the illustrative embodiments now to be described in detail in connection with the accompanying drawings. In the drawings.

It is to be understand that these drawings are for purposes of illustrating the concepts of the invention and are not to scale.

DETAILED DESCRIPTION

Figure 1:
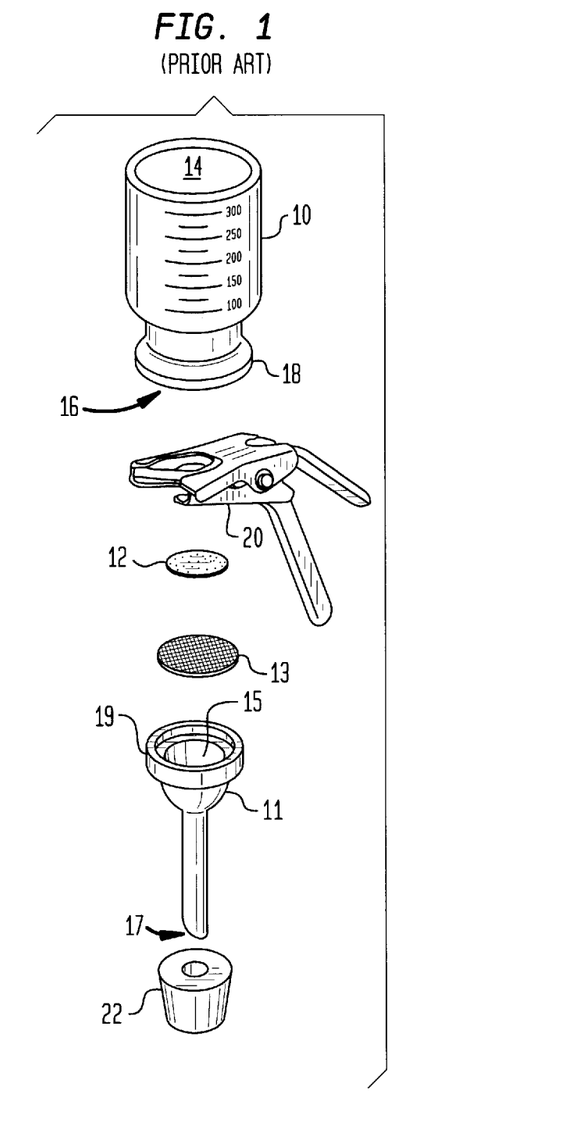
FIG. 1 is an exploded view of a conventional SPE apparatus.

The invention can be better understood by consideration of the conventional apparatus which it improves. Referring to the drawings, FIG. 1 is an exploded view illustrating a typical conventional SPE apparatus comprising a funnel 10, a base 11 and an SPE disk 12 disposed between the funnel and base on a disk support 13. Both the funnel and the base have input ports 14, 15 respectively and output ports 16, 17. The output port 16 of the funnel is provided with a flange 18, and the input port of the base has a flange 19. The SPE disk 12 is commonly a mat of glass or polymer fibers impregnated with particles of chemical separation media, for example silica gel derivatized with octadecane. The disk support 13 is typically a metal screen or a porous glass or PTFE frit. The disk and screen are clamped between the flanges 18, 19 by a two-point spring clamp 20, and the output port 17 of the base is in communication with a low pressure chamber 21 (of FIG. 2) such as a suction flask. A gasket 22 can be used to seal port 17 in relation to the chamber 21.

Figure 2:
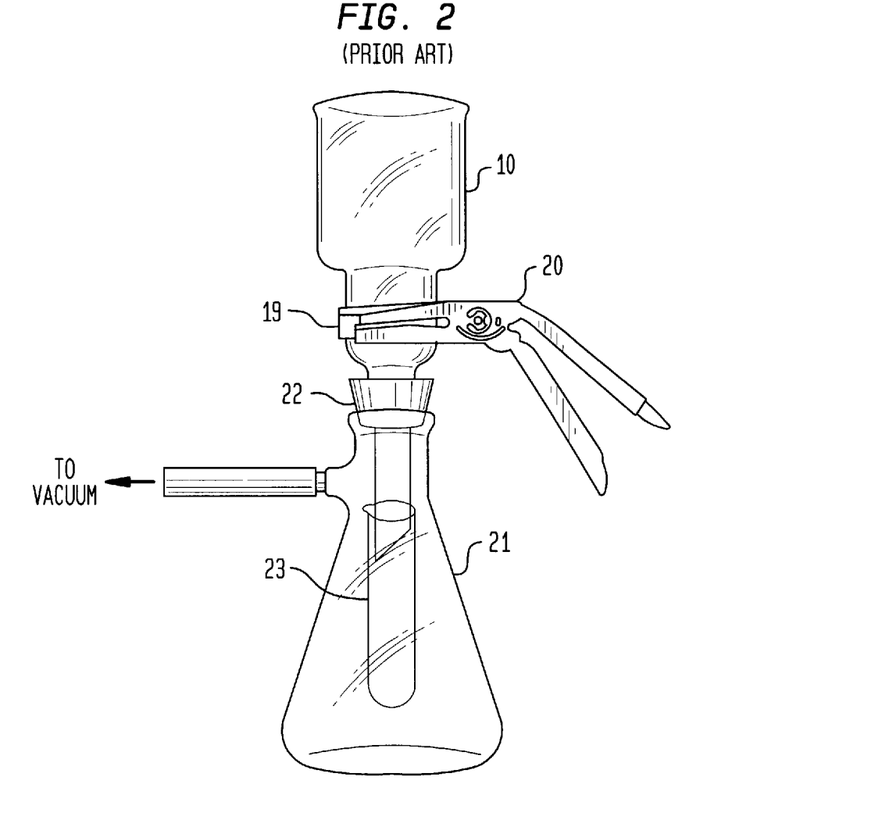
FIG. 2 shows the apparatus of FIG. 1 assembled for operation.

FIG. 2 illustrates the apparatus of FIG. 1 in typical assembled condition. The SPE disk and disk support (not visible) are placed on the base flange 19. The funnel 10 is then placed over the disk so that it is trapped around its circumference between the glass flanges of the funnel and the base. The spring clamp 20 is attached and exerts clamping pressure on two points of the assembled apparatus. The assembly is then connected via the vacuum flask 21 to a vacuum source. Optionally, collection tube 23 can be contained within low pressure chamber 21 to collect waste solvent or solvent containing the analytes of interest.

In operation, the disk is first washed with elution solvent (and activating solvent or conditioning solvent if needed). It is then wetted with a small volume of the sample to be filtered. Capillary action draws liquid into the direct flow region of the disk (the region between the openings) and into the indirect flow space between the flanges. The vacuum is turned on to initiate suction of filtrate through the disk membrane, and more sample is added to the funnel. The addition process is continued until all of the sample to be filtered has passed through the disk or the sorbent capacity of the disk is saturated.

The analytes bound by the sorbents and trapped in solids filtered out by the disk are collected by elution. The vacuum is disconnected and a small (minimal) amount of extraction solvent is applied. During a "soak" period, analytes bound by the sorbents within the disk desorb and partition into the extraction solvent. After soaking, vacuum is reapplied, and the solvent is collected. SPE analysis of a large sample may require several soak periods, particularly if solid materials are present.

While the conventional apparatus works well so long as the vacuum source is applied, analytes of interest are lost during the elution soak periods when the vacuum is removed. If the vacuum is off and there are dissolved analytes in the funnel, analyte is lost by radial wicking and weeping. Specifically, the solvent containing the analyte of interest is drawn by wicking towards the outer edges of the disk located under the glass flanges. This wicking is exacerbated under the two compression points generated by the spring clamp. Upon standing, the sample drawn to the edges will weep from the disk edges and evaporate or leak down the side of the base. Common elution solvents, such as hexane or methanol, have low viscosity and high volatility, increasing the loss of analytes. Moreover even if they do not escape from the disk, analytes that wick into the indirect flow region between the flanges partition into the sorbents in this region where they are extremely difficult to extract with a small amount of solvent. Thus analytes of interest are lost or remain adsorbed by the SPE disk and are not collected. This reduces both the total recovery and the precision of the process. This is particularly a problem if the sample contains both analytes easily dissolved or desorbed and analytes difficult to dissolve or desorb, necessitating lengthy or repeated elution steps.

Figure 3A:
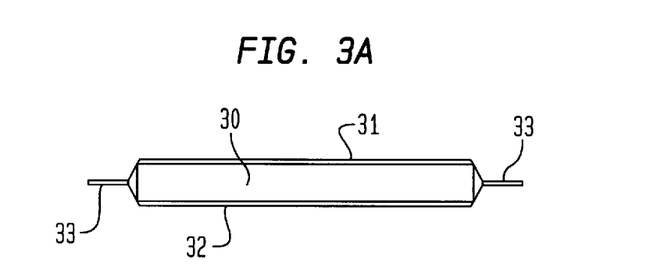
FIGS. 3A and 3B are cross sectional and top views of an SPE disk in accordance with the invention.
Figure 3B:
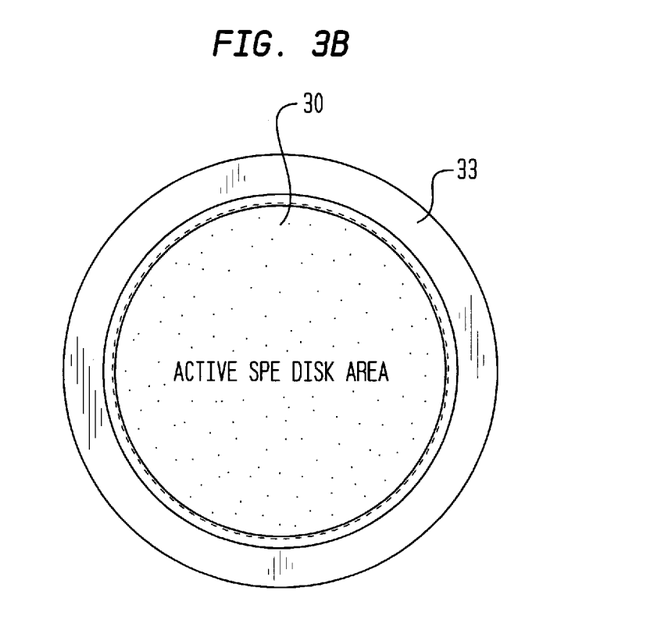

FIGS. 3A and 3B are a schematic cross section and a top view, respectively, of an improved SPE disk in accordance with the invention. The improved disk comprises a conventional SPE disk 30 encapsulated within a pair of membrane layers 31, 32. The disk 30 is dimensioned and sized within the direct flow path of a disk holder (not shown). The portions of layers 31, 32 overlying and underlying the disk in the direct flow path are porous and permit direct flow of sample through the disk. The portions of layers 31, 32 extending beyond the periphery of the disk 30 are laminated together to form an essentially non-porous rim 33 around the disk perimeter. Preferably the membrane layers are thin layers of plastic such as films of polypropylene. The pores or openings are sufficiently large, e.g. 20 micrometers, to permit liquid to easily pass into and out of the SPE disk. The disk 30 can be glass fiber or polymer fiber, such as polyethylene, containing sorbent particles.

Figure 4A:
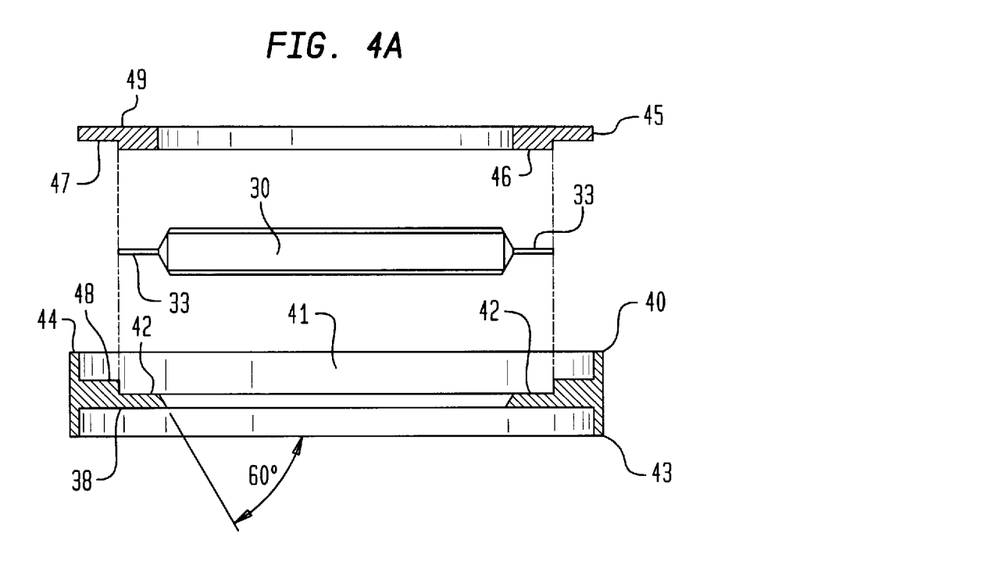
FIGS. 4A and 4B are cross sectional and top views of SPE disk holding apparatus in accordance with the invention.

FIG. 4A is a schematic cross section of an improved disk holding apparatus in accordance with the invention comprising a disk holder 40 and a ring 45. The disk holder comprises, in essence, a hollow ring having an aperture 41, a recessed region 42 surrounding the aperture on the upper surface for receiving and centering an SPE disk 30 such as the encapsulated disk of FIG. 3. In addition, the holder includes a first projecting portion 43 surrounding the aperture on the lower surface for centering the input port of the base and thereby centering the holder in relation to the port. It also includes a second projecting portion 44 on the upper surface for centering the output port of the funnel. The holder thus centers the active portion of the disk in the direct flow path of the apparatus. A second hollow ring 45 communicates with the SPE disk 30 and the holder 40 in a complementary relationship. Temporary liquid sealing of the SPE disk into the apparatus occurs at the recessed area 42 of the holder in combination with the essentially non-porous rim 34 of the SPE disk and the downward projecting portion 46 of the hollow ring 45. Additional sealing of the ring and holder takes place at the interface between surfaces 47 and 48; 49 and 18; and 38 and 19, respectively. This unique design enables a multitude of various funnels 10 to be combined with various bases 11 and still allow the active area of disk 30 to always be in the direct flow path of the apparatus. The holder and ring are preferably made of polytetrafluorethylene (PTFE).

Figure 4B:
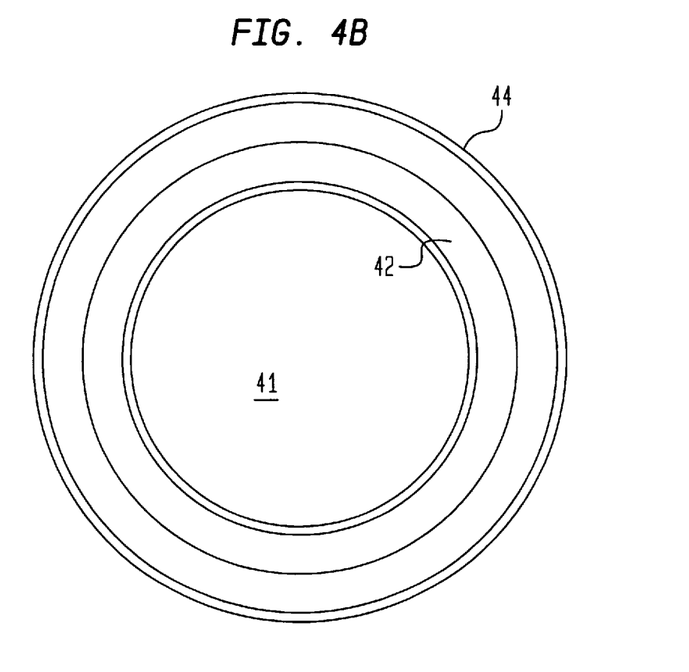

FIG. 4B is a top view of the disk holder 40.

Figure 5:
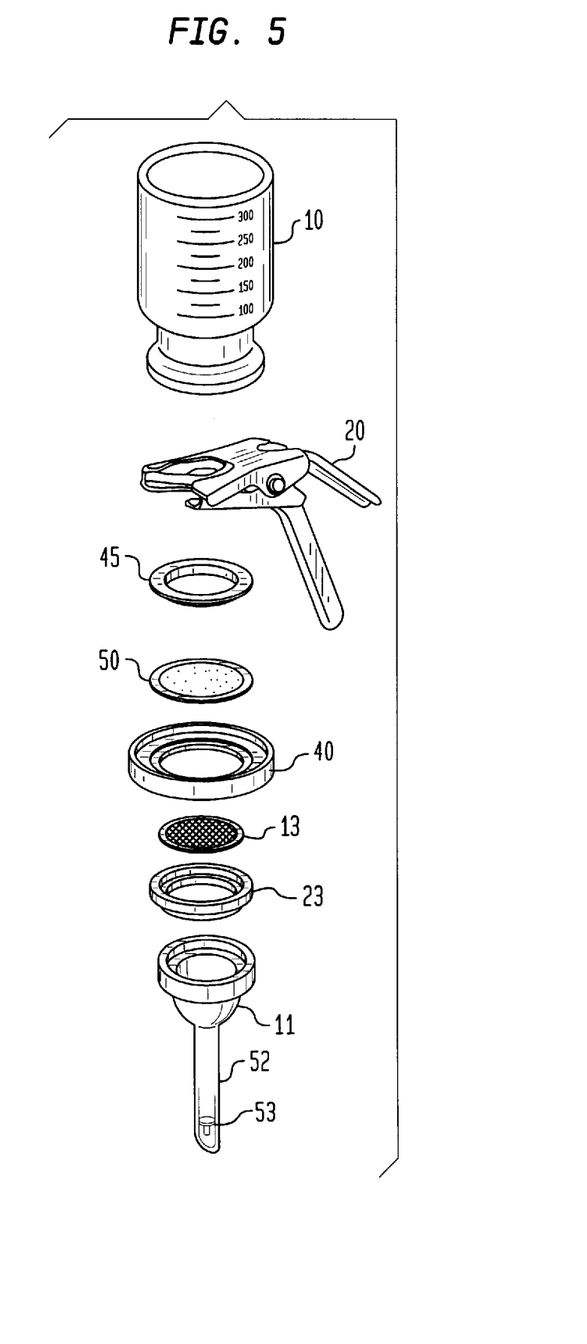
FIG. 5 is an exploded view of improved SPE apparatus in accordance with the invention.

FIG. 5 is an exploded view of a first embodiment of SPE apparatus in accordance with the invention. It differs from the conventional apparatus of FIG. 1 in that the encapsulated SPE disk 50 of FIG. 3 is held in the direct flow path by the hollow rings 45 and 40. Additionally, screen 13 may be held in place by a removable PTFE ring 23 which facilitates removal of the screen 13 from the base 11.

The advantages of this apparatus are manyfold. Because the edges of the disk are sealed in an essentially non-porous rim, loss of sample by wicking and weeping is negligible. And because the disk is held in position by clamping on the impermeable rim rather than clamping on the disk, virtually all active areas of the disk are in the direct flow path. Thus precision is also enhanced.

In most applications, the removal of water from the elute (elution solvent containing the analytes of interest) needs to occur off-line in a separate step outside the SPE apparatus. A porous filter plug 53, of polyethylene or other material, can be inserted into the neck 52 of the base 11 by interference fit. With this feature, varying amounts of drying agent, such as sodium sulfate, can be added above the plug 53, permitting in-line drying of the elute.

Figure 6:
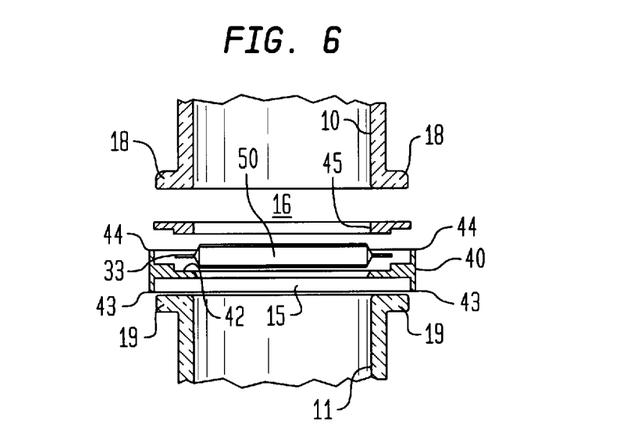
FIG. 6 shows a portion of the apparatus of FIG. 5 in assembled form.

FIG. 6 is a schematic cross section of the apparatus of FIG. 5 in assembled form. The disk 50 is supported by the holder recessed region 42, and the disk rim 33 is clamped between ring 45 and the holder 40. A spring clamp (not shown) can be used to secure the assembly together. As can be seen, projection 43 on disk holder 40 centers the support on base 11. Upper projection 44 similarly centers the support in relation to funnel 10. The disk 50, in turn, is centered in the recessed region of holder 40, thereby centering the disk in the direct flow path between funnel output port 16 and base input port 15.

Figure 7:
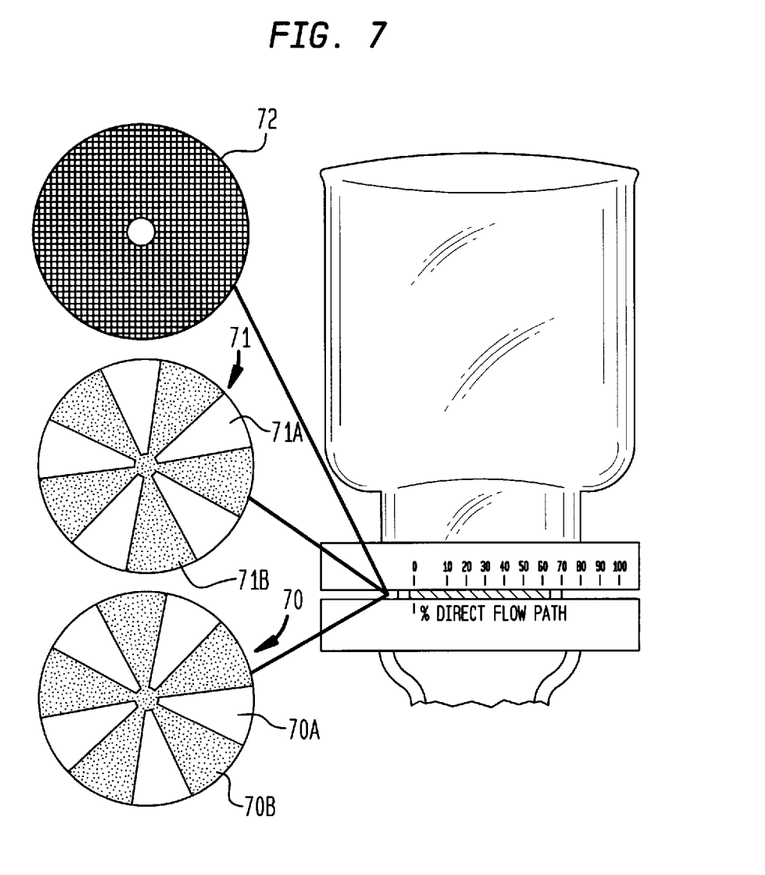
FIG. 7 illustrates an optional flow control mechanism for the disk holder.

FIG. 7 illustrates an alternative embodiment of the FIG. 4 disk holder which can be used to regulate fluid flow during extraction. In essence, the holder is modified by the presence of three disks. The bottom disk 70, which can be stationary, is a disk with alternatively permeable (open) sectors 70A and impermeable (closed) sectors 70B. In the embodiment illustrated there are 10 sectors each encompassing 36° of the disk circumference. The middle disk 71, which can be movable, is also divided into open and closed sectors. The top disk 72 can be a permeable screen for supporting the SPE disk to keep it from being blinded by middle disk 71. In operation, rotation of disk 71 in relation to disk 70 can change the rate of flow from 100% through the device (corresponding to overlap of the impermeable sectors) to 0% (corresponding to the impermeable sectors overlapping the permeable ones). Alternatively, by varying the size of the sectors in one of the disks so that complete overlap of impermeable sectors does not occur, one can regulate flow over a smaller range. This permits control of both liquid flow and the presence or absence of suction applied to the SPE disk.

Figure 8:
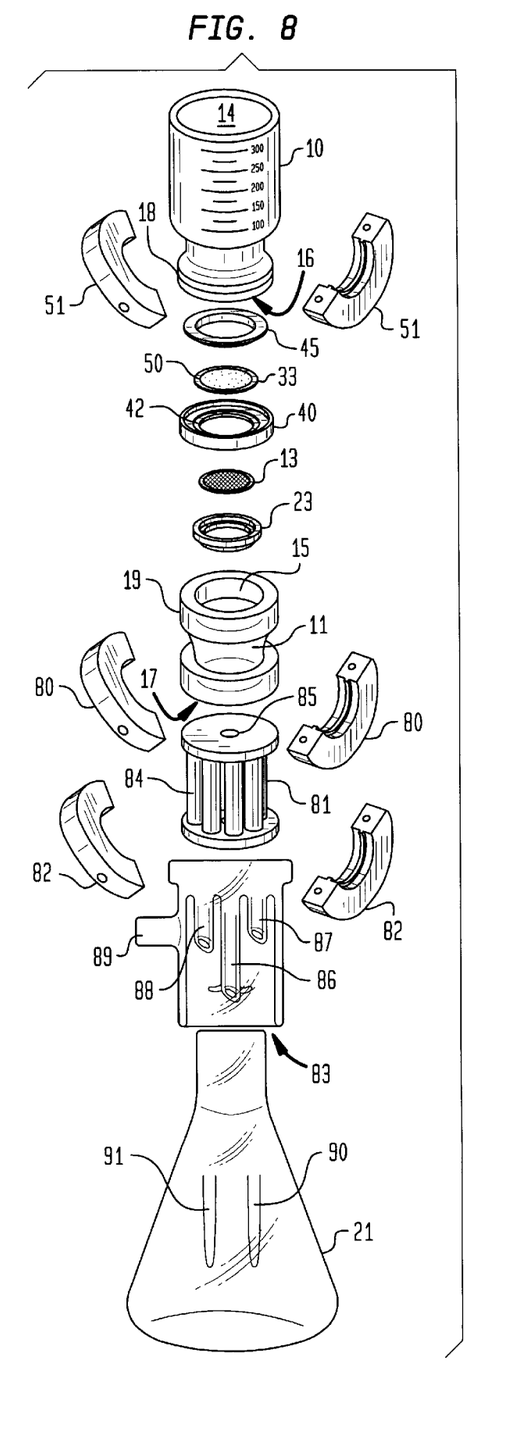
FIG. 8 is an exploded view of a second embodiment of improved SPE apparatus.

FIG. 8 illustrates a preferred embodiment of a SPE apparatus, including disk and holder, shown in an assembled form. This design is optimized for enhanced recovery and precision.

In some applications, such as analysis of oil and grease, particularly when solid trapped on top of the SPE disk contains analytes, it is beneficial to extend the soaking time in which the disk and solid are immersed in elution solvent. This extension is difficult in the standard apparatus because solvent drains through the disk into the collection tube, even without vacuum.

A funnel 10 with threaded flanges 18 is assembled to SPE disk/holders assembly 40, 45 and 50 and secured. The utilization of external threads on the glassware and mating internal threads on the PTFE flow regulators/directors eliminates the use of traditional clamps 20 and makes the design more rugged and capable of providing the enhanced features described below. Screen 13 is inserted into ring 23 and placed into base 11 which is then assembled to SPE disk/holders assembly 40, 45 and 50 via the thread flanges on the base 19. Similarly, connections between base 11 and flow distributor 80, flow distributor 82 and vacuum port assembly 82 are all in communication with each other via threaded connections. Once the apparatus is assembled, collection tube 90 and waste tube 91 are inserted. The assembled apparatus is then inserted into low pressure receiver 21 and sealed via a ground glass joint at area 83. After the device is assembled and properly loaded with drying agent in the multiple drying columns 84, it does not need to be disassembled again until the test is completed. The SPE disk 50 and collection tube 90, waste tube 91, and flask 21 are then emptied or changed to initiate a new test. This is a major improvement in reducing the number of manual transfers and apparatus assembly/disassembly steps that would need to occur in a typical SPE disk method.

In the preferred embodiment, the apparatus should be assembled only initially and be disassembled only when the test is complete and the collection tube needs to be removed. In addition, the vacuum is also only turned on once initially and turned off at the source when the apparatus is finally disassembled. All other vacuum/flow control requirements are achieved by the flow control/flow diverter mechanisms 51, 80 and 82. In addition, initial experiments indicate that elution solvent requirements are reduced by the utilization of precisely controlled exposures of the SPE disk to vacuum and elution solvent. The response time from a traditional apparatus is too slow and the vacuum force in the area of the SPE disk is uncontrollable.

It is to be understood that the above-described embodiments are illustrative of only a few of the many possible specific embodiments which can represent applications of the principles of the invention. The improvements herein applicable to the manual utilization of the apparatus are also applicable to automated equipment. In addition, these enhancements can also be used with the traditional SPE columns using a vacuum manifold box. Numerous and varied other arrangements can be made by those skilled in the art without departing from the spirit and scope of the invention.

What is claimed:

1. In a solid phase extraction (SPE) apparatus comprising a first hollow body having an input port and an output port, a second hollow body having an input port, and disposed between the output port of said first body and the input port of said second body, a SPE disk and a holder for said SPE disk, said disk positioned for filtering sample placed in said first body, the improvement wherein:

said SPE disk comprises a fiber matrix containing sorbent material, said matrix encapsulated between porous outer polymeric layers united into a rim extending beyond said matrix around the perimeter of said matrix; and said holder comprises a first hollow ring and a second ring member, said first hollow ring having an inner peripheral recessed region for supporting and centering said SPE disk and an outer projecting peripheral region for centering said first body, said second ring member sized and dimensioned for clamping said rim of said SPE disk against said first hollow ring said SPE disk thereby centered within the output port of said first body.

2. The improved SPE apparatus of claim 1 wherein said second ring member includes a projecting region sized and dimensioned for clamping said rim of said SPE disk against said first ring, thereby supporting said disk without clamping said matrix.

3. The improved SPE apparatus of claim 1 wherein said holder comprises polytetrafluoroethylene.

4. The improved SPE apparatus of claim 1 wherein said holder further comprises a fluid flow controller.

5. The improved SPE apparatus of claim 4 wherein said fluid flow controller comprises a rotatable disk having alternating permeable and impermeable sectors and a non-rotatable disk having alternating permeable and impermeable sectors.

6. The improved SPE apparatus of claim 1 wherein said first body comprises threaded flanges and said holder comprises a ring having a threaded region for receiving said threaded flanges, thereby permitting threaded connection between said first body and said holder.

* * * * *